US009715757B2

(12) United States Patent
Ng et al.

(10) Patent No.: US 9,715,757 B2
(45) Date of Patent: Jul. 25, 2017

(54) ULTRASOUND IMAGING SYSTEM AND METHOD FOR IMAGE GUIDANCE PROCEDURE

(71) Applicant: KONINKLIJKE PHILIPS N.V., Eindhoven (NL)

(72) Inventors: Gary Cheng-How Ng, Redmond, WA (US); James Robertson Jago, Seattle, WA (US); Andrew Lee Robinson, Bellevue, WA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 14/403,288

(22) PCT Filed: May 28, 2013

(86) PCT No.: PCT/IB2013/054405
§ 371 (c)(1),
(2) Date: Nov. 24, 2014

(87) PCT Pub. No.: WO2013/179224
PCT Pub. Date: Dec. 5, 2013

(65) Prior Publication Data
US 2015/0294497 A1    Oct. 15, 2015

Related U.S. Application Data
(60) Provisional application No. 61/653,506, filed on May 31, 2012.

(51) Int. Cl.
*G06T 15/08* (2011.01)
*G06T 11/00* (2006.01)
(Continued)

(52) U.S. Cl.
CPC ............ *G06T 15/08* (2013.01); *A61B 8/0891* (2013.01); *A61B 8/4263* (2013.01); *A61B 8/466* (2013.01);
(Continued)

(58) Field of Classification Search
None
See application file for complete search history.

(56) References Cited

U.S. PATENT DOCUMENTS

| 7,925,327 B2 | 4/2011 | Weese |
| 7,970,189 B2 | 6/2011 | Buelow et al. |

(Continued)

FOREIGN PATENT DOCUMENTS

| CN | 101478917 A | 7/2009 |
| CN | 191523438 A | 9/2009 |

(Continued)

OTHER PUBLICATIONS

Porter, Brian C., et al. "Three-dimensional registration and fusion of ultrasound and MRI using major vessels as fiducial markers." Medical Imaging, IEEE Transactions on 20.4 (2001): 354-359.*

(Continued)

*Primary Examiner* — Vikkram Bali
*Assistant Examiner* — Tracy Mangialaschi

(57) ABSTRACT

The present invention relates to an ultrasound imaging system (10) comprising an ultrasound probe (20) having a transducer array (21) configured to provide an ultrasound receive signal. The system further comprises a B-mode volume processing unit (30) configured to generate a B-mode volume (31) based on the ultrasound receive signal, and a B-mode image processing unit (40) configured to provide a current B-mode image (41) based on the B-mode volume (31). The system further comprises a memory (50) configured to store a previously acquired 3D-vessel map (Continued)

(51). Also, the system comprises a registration unit (60) configured to register the previously acquired 3D-vessel map (51) to the B-mode volume (31) and to select a portion (61) of the 3D-vessel map corresponding to the current B-mode image (41). Further, the system comprises a display configured to display an ultrasound image (71) based on the current B-mode image (41) and the selected portion (61) of the 3D-vessel map (51). The present invention further relates to a method for providing such ultrasound image with vessel information and a corresponding computer program.

12 Claims, 12 Drawing Sheets

(51) Int. Cl.
  *A61B 8/06* (2006.01)
  *A61B 8/08* (2006.01)
  *A61B 8/00* (2006.01)
  *A61B 34/20* (2016.01)
  *A61B 90/00* (2016.01)

(52) U.S. Cl.
  CPC ............ *A61B 8/483* (2013.01); *A61B 8/5246* (2013.01); *A61B 8/5261* (2013.01); *A61B 34/20* (2016.02); *G06T 11/003* (2013.01); *A61B 8/06* (2013.01); *A61B 8/0841* (2013.01); *A61B 8/4245* (2013.01); *A61B 8/4405* (2013.01); *A61B 8/461* (2013.01); *A61B 8/467* (2013.01); *A61B 8/488* (2013.01); *A61B 2034/2051* (2016.02); *A61B 2034/2061* (2016.02); *A61B 2034/2063* (2016.02); *A61B 2034/2065* (2016.02); *A61B 2090/378* (2016.02)

(56) References Cited

U.S. PATENT DOCUMENTS

| 2006/0020204 A1 | 1/2006 | Serra et al. |
|---|---|---|
| 2007/0073152 A1 | 3/2007 | Washburn |
| 2008/0247622 A1* | 10/2008 | Aylward ............... A61B 90/36 382/131 |
| 2010/0061603 A1 | 3/2010 | Mielekamp et al. |
| 2010/0063400 A1* | 3/2010 | Hall et al. .................... 600/466 |
| 2010/0099979 A1 | 4/2010 | Schoonenberg et al. |
| 2011/0051885 A1* | 3/2011 | Buelow ................. G06T 7/0028 378/4 |
| 2011/0246129 A1 | 10/2011 | Ishikawa et al. |
| 2011/0263985 A1 | 10/2011 | Gauthier |
| 2012/0238875 A1* | 9/2012 | Savitsky ............... A61B 8/4254 600/443 |

FOREIGN PATENT DOCUMENTS

| EP | 2160978 A1 | 3/2010 |
|---|---|---|
| JP | 07204203 A | 8/1995 |
| JP | 07213522 A | 8/1995 |
| JP | 2008529641 A | 8/2008 |
| JP | 2009022459 A | 2/2009 |
| JP | 2011011001 A | 1/2011 |
| RU | 2286714 C1 | 11/2006 |
| WO | 2009028354 A1 | 3/2009 |

OTHER PUBLICATIONS

Lange, Thomas, et al. "Augmenting intraoperative 3D ultrasound with preoperative models for navigation in liver surgery." Medical Image Computing and Computer-Assisted Intervention—MICCAI 2004 (2004): 534-541.*
Nam, Woo Hyun, et al. "Robust registration of 3-D ultrasound and CT images of the liver for image-guided intervention." Biomedical Imaging: From Nano to Macro, 2010 IEEE International Symposium on. IEEE, 2010.*
"Three-Dimensional Registration and Fusion of Ultrasound" Porter et al, IEEE Transactions on Medical Imaging, 2001, p. 354-359.
"Automatic Non-Linear Mapping of Pre-Procedure CT Volumes To 3d Ultrasound" Wein et al, Biomedical Imaging, IEEE International Symposium, 2010 p. 1225-1228.

* cited by examiner

ULTRASOUND IMAGING SYSTEM AND METHOD FOR IMAGE GUIDANCE PROCEDURE

This application is the U.S. National Phase application under 35 U.S.C. §371 of International Application No. PCT/IB2013/054405, filed on May 28, 2013, which claims the benefit of U.S. Provisional Application No. 61/653506 filed on May 31, 2012. These applications are hereby incorporated by reference herein.

FIELD OF THE INVENTION

The present invention relates to an ultrasound imaging system and a method for providing an ultrasound image with vessel information, in particular for use in an image guidance procedure. The present invention further relates to a computer program for implementing such method.

BACKGROUND OF THE INVENTION

In three-dimensional (3D) ultrasound imaging, also called volume imaging, the acquisition of a 3D-image is accomplished by conducting many two-dimensional (2D) scans that slice the volume of interest in an anatomical region. Hence, a multitude of 2D-images is acquired that lie one next to one another. This multitude of 2D-images together forms a 3D-volume of data. By proper image processing, a 3D-image of the volume of interest can be built out of the 3D-volume of data. The 3D-image can then be displayed in a proper form on a display for the user of the ultrasound imaging system.

Ultrasound imaging is commonly used to image the insertion, use or operation of an invasive medical device or instrument within the body. For example, fine needle aspiration (FNA), core biopsy, radio frequency ablation (RFA), percutaneous ethanol injection (PEI) are all procedures that require insertion of an invasive medical device into the patient. Such a procedure using ultrasound imaging is commonly referred to as ultrasound image guidance procedure. When performing such image guidance procedure, the doctor must be able to visualize the target (e.g. a carcinoma to be ablated in RFA) in the anatomical region, the invasive medical device (e.g. needle) approaching the target, and any vessels surrounding the target, in particular blood vessels (also called vasculature). Imaging of the vessels is key for ensuring that no major vessel is punctured during the insertion and guidance of the invasive medical device. Therefore, the doctor or clinician commonly relies on using ultrasound image guidance to insert an invasive medical device, such as a biopsy needle or an ablation probe, into a patient, for both diagnosis and treatment. Ultrasound image guidance is important because it helps the doctor or clinician to visualize and hence plan the path of the invasive medical device from the skin to the target (e.g. target lesion), while avoiding blood vessels along the way.

Most of the ultrasound image guidance is done under 2D B-mode ultrasound. This is primarily because frame rates are high in 2D B-mode ultrasound. B-mode generally refers to a mode of operation in which the display shows a grayscale image representing the 2-dimensional distribution of ultrasound backscatter amplitude from one plane or slice of the target, which is formed by detecting the returning echoes for each of a series of acquisition lines across the image plane (typically one transmit pulse per line). It is quite critical to reduce any time lag between what is shown on the display and what is actually happening with the invasive medical device (e.g. needle) in the patient's body. A slow frame rate and accordingly a delayed ultrasound image feedback may result in the invasive medical device (e.g. needle) missing in the intended anatomical region. This can limit the use of any flow imaging techniques, which require the acquisition of many pulse-echo events per imaging line, such as for example color flow imaging or also called color Doppler imaging, during an ultrasound image guiding procedure. On the other hand, flow imaging provides a far better delineation of the vessel boundaries than the B-mode alone. In particular, 3D-flow imaging would be a good method for ensuring that vessels do not lie in the path of the invasive medical device (e.g. needle) since in 2D-imaging only a single plane is seen and it is typically difficult to keep the invasive medical device in the plane of the image at all times. However, frame rates in 3D-imaging, and especially 3D-flow imaging, are usually even more compromised than in the 2D-imaging.

US 2011/0263985 A1 discloses an ultrasound imaging system for creating simultaneous needle and vascular blood flow color Doppler imaging. A B-mode image of an anatomical area of interest is created. A first set of Doppler image data optimized for the visualization of vascular blood flow is created along one Doppler image processing path. A second set of Doppler image data optimized for the visualization of a needle or other invasive device is created among another, parallel Doppler image processing path. The color Doppler image is created, and then displayed, by combing some or all of the B-mode images, the first Doppler image data and the second Doppler image data based on a plurality of user selectable modes.

Such ultrasound imaging system uses B-mode ultrasound imaging and color Doppler imaging simultaneously. This reduces the frame rate. Therefore, there is a need for increasing or providing a sufficient frame rate in ultrasound image guidance procedures.

SUMMARY OF THE INVENTION

It is an object of the present invention to provide an improved ultrasound imaging system, in particular with increased or sufficient frame rate. It is a further object of the present invention to provide an improved method for providing an ultrasound image with vessel information, in particular at an increased or sufficient frame rate, and a corresponding computer program for implementing such method.

In a first aspect of the present invention, an ultrasound imaging system is presented that comprises an ultrasound probe having a transducer array configured to provide an ultrasound receive signal, a B-mode volume processing unit configured to generate a B-mode volume based on the ultrasound receive signal, a B-mode image processing unit configured to provide a current B-mode image based on the B-mode volume, a memory configured to store a previously acquired 3D-vessel map, a registration unit configured to register the previously acquired 3D-vessel map to the B-mode volume and to select a portion of the 3D-vessel map corresponding to the current B-mode image, and a display configured to display an ultrasound image based on the current B-mode image and the selected portion of the 3D-vessel map.

In a further aspect of the present invention, a method for providing an ultrasound image with vessel information is presented, the method comprising: receiving an ultrasound receive signal provided by an ultrasound probe having a transducer array, generating a B-mode volume based on the ultrasound receive signal, providing a current B-mode image based on the B-mode volume, registering a previously acquired 3D-vessel map stored in a memory to the B-mode volume, selecting a portion of the 3D-vessel map corresponding to the current B-mode image, and providing the ultrasound image based on the current B-mode image and the selected portion of the 3D-vessel map.

In a further aspect of the present invention, a computer program is presented comprising program code means for causing a computer to carry out the steps of such method when said computer program is carried out on the computer.

It can be assumed that B-mode volumes, or also called 3D B-mode, has acceptable frame rates (or volume rate), but simultaneous 3D B-mode and 3D color flow imaging does not. This invention can provide a way to have the benefits of both 3D B-mode and 3D color flow at the 3D B-mode frame rates.

The basic idea of the invention is to acquire or create a 3D-vessel map at the beginning or before an ultrasound image guidance procedure. Thereafter, this 3D-vessel map is registered to the B-mode volume. Preferably, the 3D-vessel map is updated as the ultrasound image guidance procedure takes place. In particular, a 3D vessel map is acquired and stored in a memory in a first step. Since the 3D-vessel map is acquired at the beginning of the ultrasound image guidance procedure, prior to actually inserting the invasive medical device (e.g. needle), into the patient, time can be taken to acquire the highest possible quality 3D-vessel map. During the ultrasound image guidance procedure, the 3D-vessel map is registered, and preferably tracked (i.e. continuously updating the registration), with the current or live B-mode image (e.g. 2D- or 3D-image). The frame rates during the acquisition of the 3D-vessel map may be slow, but since the 3D-vessel map is acquired at the beginning or before of an ultrasound image guidance procedure, the frame rate during the ultrasound image guidance procedure itself, using B-mode imaging, is not affected. Thus, since the current or live acquisition of ultrasound images only involves B-mode, high or real-time frame rates can be achieved. Also, the doctor or user is still able to see the vessel information (e.g. vessel outlines) overlaid on the B-mode image which helps to avoid the vessels during the image guidance procedure. Therefore, the present invention allows for fast frame rates, in particular needed for image guidance procedures using an invasive medical device (e.g. needle), and yet allows a 3D-vessel map or its corresponding vessel information to be used to highlight regions to avoid in the ultrasound image.

Preferred embodiments of the invention are defined in the dependent claims. It shall be understood that the claimed method or computer program have similar and/or identical embodiments as the claimed ultrasound imaging system and as defined in the dependent claims.

In one embodiment, the current B-mode image is a 2D-image, an image of orthogonal 2D-image planes or a 3D-image. Even though a B-mode volume, thus 3D data, is generated the actual presentation or displaying of data on a display may be different. For example, the system may only display a 2D-image or slice out of that volume in any suitable way (e.g. regular 2D-image or orthogonal 2D-image planes). When the current B-mode image (to be displayed) is a 2D image or a 3D-image of orthogonal 2D-image planes (e.g. Multi-Planar Reformatted (MPR)), an easier presentation of the ultrasound image is provided compared to a 3D representation. Alternatively, the current B-mode image (to be displayed) can of course also be a 3D-image, which provides the most information to the user and thus increases performance of the system.

In another embodiment, the portion is a 2D-slice of the 3D-vessel map. This embodiment is in particular used when the current B-mode image is a 2D-image, or an image of orthogonal 2D-image planes. If the B-mode volume is sliced to get a 2D-slice or 2D-image to be displayed, also the 3D-vessel map can be sliced in the same way.

In an alternative embodiment, the portion is a 3-D portion of the 3D-vessel map. This embodiment is in particular used when the current B-mode image is a 3D-image. If a 3D-image is to be displayed, also the 3D-vessel map can be superimposed in the same way. For example, the 3D B-mode image can be semi-transparent to allow the 3D-vessel map (e.g. in color) to be visible.

In a further embodiment, the ultrasound imaging system comprises an image processing unit configured to overlay the current B-mode image and the selected portion of the 3D-vessel map to provide the ultrasound image. In this way an ultrasound image with overlaid vessel information is generated and displayed. Thus the vessel information or portion of the 3D-vessel map is directly overlaid onto or incorporated into the ultrasound image. This improves legibility of the information for the user of the system (e.g. doctor or clinician), during an image guidance procedure for example. In this way a very intuitive (or most intuitive) display is provided. The corresponding method comprises the further step of overlaying the current B-mode image and the selected portion of the 3D-vessel map to provide the ultrasound image.

In an alternative embodiment, the ultrasound imaging system comprises an image processing unit configured to add the current B-mode image and the selected portion of the 3D-vessel map next to each other to provide the ultrasound image with vessel information. In this way, the ultrasound image is provided by having the current (or live) B-mode image and the selected portion of the 3D-vessel map in a side by side format or representation. For example, the current (or live) B-mode image is presented as a first image portion on the right side of the display and the selected portion is presented in a second image portion on the left side of the display. The selected portion or vessel information can for example be in a previously acquired registered image (e.g. color image). For example, the selected portion can be presented or contained in CT data or MR data, or in an ultrasound image.

In another embodiment, the ultrasound imaging system comprises a 3D flow processing unit configured to generate 3D flow data based on the ultrasound receive signal, and a flow image processing unit configured to generate the 3D vessel map based on the 3D flow data. In this case the vessels or vasculature in the anatomical region are identified using a 3D flow imaging technique. This is a particularly reliable and/or high-quality ensuring way of identifying the vessels and providing a 3D-vessel map. 3D flow imaging can provide a high quality 3D color flow image or 3D vessel map. The frame rates may be slow, but since the 3D flow imaging is performed at the beginning or before of an ultrasound image guidance procedure, the frame rate during the ultrasound image guidance procedure is not effected. The 3D flow data can also be called a flow volume. For example, 3D flow data or flow volume can be generated in that the transducer array transmits multiple ultrasound pulses for each line (to estimate the flow at that line or location), and then the acquisition of these lines is swept across the volume. The number of ultrasound pulses may be increased.

This increases the sensitivity, but also reduces the frame rates. The corresponding method comprises the further steps of generating 3D flow data based on the ultrasound receive signal, and generating the 3D vessel map based on the 3D flow data.

In a variant of this embodiment, the 3D flow data is generated using a color flow technique, a Color Power Angio (CPA) technique, a B-mode flow imaging technique or a Contrast Enhanced Ultrasound technique. These are particularly suitable ways of providing a flow image. In the case of CPA, the generated flow image indicates only the magnitude of the flow, and not directionality of the flow. Thus, this technique is a particularly easy way of providing a flow image, while still providing sufficient information about the vessels. In the case of B-mode flow imaging (also called B-flow), the flow image is generated using a B-mode pulse subtraction technique. This technique provides flow imaging at a higher frame rate than a traditional color flow technique. A Contrast Enhanced Ultrasound technique is a particularly suitable way to improve the visualization of the vessels, especially in technically challenging cases.

In another variant of this embodiment, the ultrasound imaging system comprises a controller configured to select either the B-mode volume processing unit to generate the B-mode volume or the 3D flow processing unit to generate the 3D flow data. In this way it can be easily implemented to first acquire a 3D-vessel map before or at the beginning of an image guidance procedure, and to the subsequently use B-mode imaging during the image guidance procedure. For example, the controller can be configured to select the 3D flow processing unit when receiving a first input from a user control (e.g. when a user hits a "Start" button) and to select the B-mode volume processing unit when receiving a second input from the user control (e.g. when the user hits an "Accept" button). For example, when the controller selects the 3D flow processing unit, 3D flow data can be generated in that the transducer array transmits multiple ultrasound pulses for each line, and then the acquisition of these lines is swept across the volume. For example, when the controller selects the B-mode volume processing unit, a B-mode volume can be generated in that the transducer array transmits a single pulse for each line, and then the acquisition of these lines is swept across the volume. The corresponding method comprises the further step of selecting either the B-mode volume processing unit to generate the B-mode volume or the 3D flow processing unit to generate the 3D flow data.

In another embodiment, the ultrasound imaging system comprises a vessel segmentation unit configured to create the 3D-vessel map by performing a vessel segmentation technique. In this case the vessels or vasculature in the anatomical region are identified using a vessel segmentation technique. This is a particularly easy and/or reliable way of identifying the vessels and providing a 3D-vessel map. It eliminates the need to perform flow imaging, which may be challenging in some clinical situations or patients. In the corresponding method the step of creating the 3D-vessel map comprises performing a vessel segmentation technique.

In a variant of this embodiment, the vessel segmentation unit is configured to perform the vessel segmentation technique based on the B-mode volume. In this case the 3D-vessel map is created based on 3D ultrasound data, namely the B-mode volume data that the system needs to acquire anyway. This provides for a particular easy way of creating the 3D-vessel map without the use of any other system or data. The B-mode volume can for example be conventional 3D ultrasound data or contrast enhanced 3D ultrasound data. In the corresponding method the vessel segmentation technique is performed based on the B-mode volume.

In another variant of this embodiment, the vessel segmentation unit is configured to perform the vessel segmentation technique based on CT data or MR data. In this case the 3D-vessel map is created based on CT or MR data, in particular received from a separate CT or MR system. This provides for a particular reliable way of creating the 3D-vessel map as the CT or MR data can be easier to segment than ultrasound data, especially when a CT or MR contrast agent is used. The CT data can for example be conventional CT data, cone beam CT data, or CT angiography data. The MR data can for example be conventional MR data or MR Angiography data. The CT or MR data may be acquired with or without a contrast agent. In the corresponding method the vessel segmentation technique is performed based on based on CT data or MR data.

In yet another embodiment, the registration unit is configured to receive ultrasound transducer position tracking information for selecting the portion of the 3D-vessel map corresponding to the current B-mode image. The ultrasound transducer position tracking information indicates and/or tracks the position of the ultrasound probe having the transducer array, or also called ultrasound transducer. In this way the registration can be continuously updated, which increases reliability and usability of the system. In particular, as the ultrasound probe or transducer is moved when scanning the patient, the doctor can see and track in real-time the invasive medical device and the vessels in relation thereto. The corresponding method comprises the further step of receiving ultrasound transducer position tracking information, and wherein the selection step comprises selecting the portion using the ultrasound transducer position tracking information.

In a variant of this embodiment, the ultrasound imaging system further comprises a processing unit configured to generate the ultrasound transducer position tracking information based on temporally consecutive B-mode volumes. In particular, the ultrasound transducer position tracking information can be translation and/or rotation information. In this case the ultrasound transducer position tracking information is provided based on 3D ultrasound data, namely the B-mode volume data that the system needs to acquire anyway. This provides for a particular easy way of generating ultrasound transducer position tracking information without the use of any other device or devices. This use of temporally consecutive B-mode volumes to generate the ultrasound transducer position tracking information is also called image-based tracking. When having 3D ultrasound volumes consecutive in time, the translation or rotation of features in these B-mode volumes can be tracked and based thereon a translation vector or rotation vector can be extracted. Thus, the processing unit can be configured to perform feature tracking on the temporally consecutive B-mode volumes and to generate a translation or rotation vector based on the feature tracking. This translation or rotation vector can then be used for selecting the appropriate portion of the 3D-vessel map. The term temporally consecutive can refer to B-mode volumes being acquired directly following each other or can refer to B-mode volumes being acquired not directly following each other, thus being spaced apart in time (e.g. only every other or every third volume). The corresponding method comprises the further step of generating the ultrasound transducer position tracking information based on temporally consecutive B-mode volumes.

In a further variant of this embodiment, the ultrasound imaging system further comprises a position sensor which is positioned in fixed known position with respect to the transducer array. The ultrasound transducer position tracking information is position information received from the position sensor. This provides for a particular easy way of generating ultrasound transducer position tracking information which does not require any additional signal processing. In particular, the position information can be orientation and/or positional change of the ultrasound probe and thus the transducer array. The position sensor can for example be arranged in fixed known position with respect to the ultrasound probe having the transducer array, for example arranged on or attached to the housing on the probe. For example, the position sensor can be an electromagnetic (EM) tracking sensor or a fiber optic tracking sensor, or any other sensor that provides tracking information about the transducer position. The corresponding method comprises the further step of receiving the ultrasound transducer position tracking information from a position sensor which is positioned in fixed known position with respect to the transducer array.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
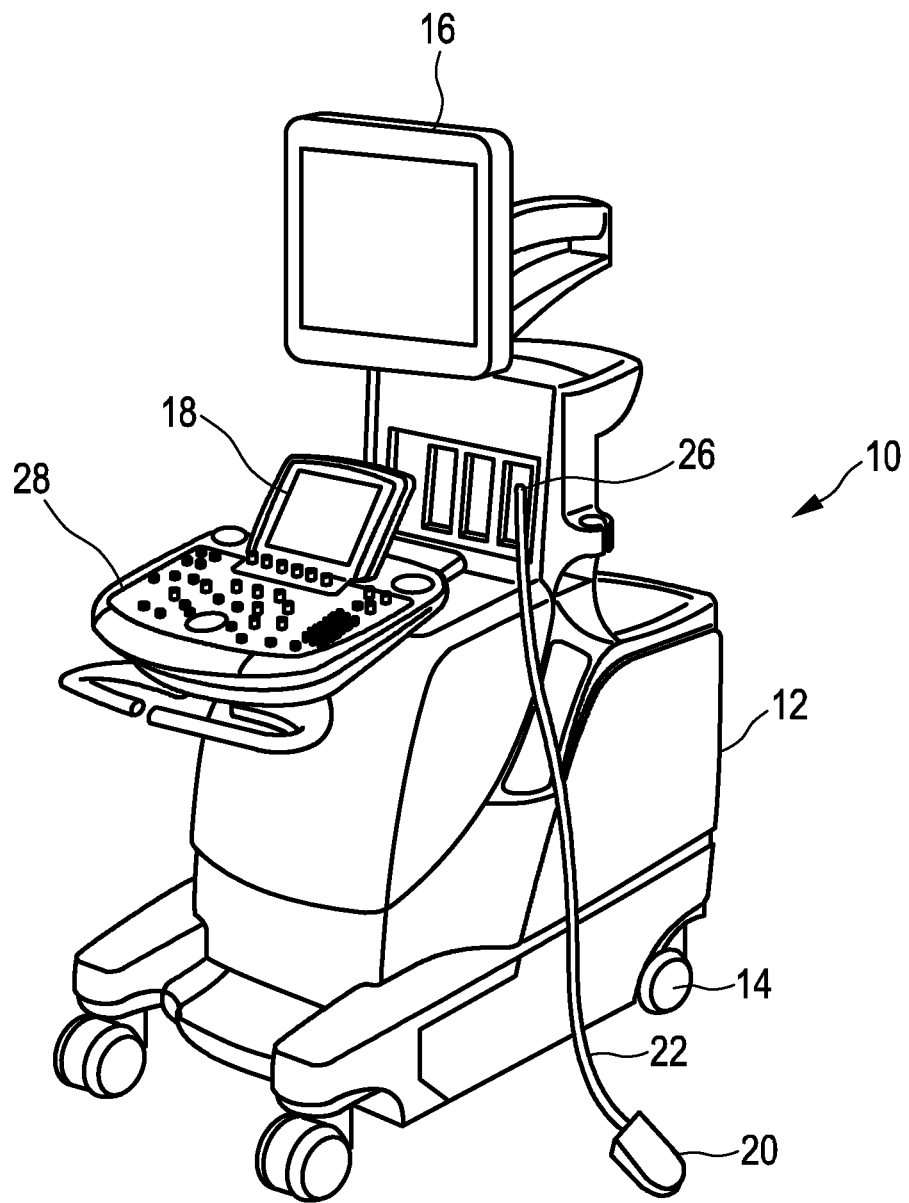
FIG. 1 shows a perspective view of an ultrasound imaging system according to an example.

FIG. 1 shows a perspective view of an ultrasound imaging system 10 according to an example. The system 10 includes a chassis 12 containing most of the electronic circuitry for the system 10. The chassis 12 may be mounted on a cart 14, and a display 16 is mounted on the chassis 12. An ultrasound probe 20 may be connected through a cable 22 to one of connectors 26 on the chassis 12. The chassis 12 includes a keyboard and user controls, generally indicated by reference numeral 28, for allowing a doctor or sonographer to operate the ultrasound system 10 and enter information about the patient or the type of examination that is being conducted. At the back of the control panel or user controls 28 is a touchscreen display 18 on which programmable softkeys may be displayed for supplementing the keyboard and controls 28 in controlling the operation of the system 10. The chassis 12 generally also includes a pointing device such as a trackball that may be used to, for example, manipulate an on-screen pointer. The chassis 12 may also include one or more buttons (not shown) which may be pressed or clicked after manipulating the on-screen pointer. These operations are analogous to a mouse being used with a computer. In operation, the imaging probe 20 having a transducer array therein is placed against the skin of a patient (not shown) and held stationary to acquire an image of blood or tissue in a 2D or 3D anatomical region beneath the skin. The image is presented on the display 16, and it may be recorded by a recorder (not shown), which is for example placed on an accessory shelf of the chassis. The system 10 may also record or print a report containing text and images. Data corresponding to the image may also be downloaded through a suitable data link, such as the Internet or a local area network.

It will be understood that the ultrasound imaging system 10 of FIG. 1 is merely illustrative and that any other suitable ultrasound imaging system can be used. In one example, the ultrasound imaging system can have a X6-1 ultrasound transducer/probe or a C5-1 ultrasound transducer/probe, which is currently distributed by Philips. In another example, the ultrasound imaging system can additionally have EM position sensing, such as PercuNav, which is currently distributed by Philips.

Figure 2:
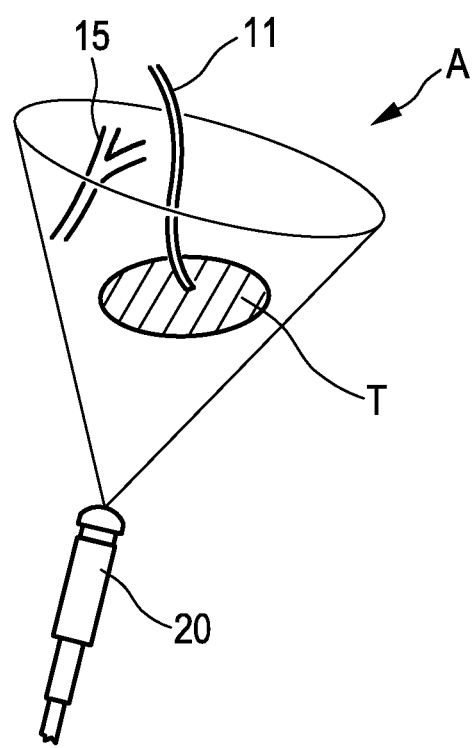
FIG. 2 shows a schematic diagram of an exemplary ultrasound probe imaging an anatomical region in an image guidance procedure.

FIG. 2 shows a schematic diagram of an exemplary ultrasound probe 20 imaging an anatomical region A in an image guidance procedure. Here, the ultrasound probe 20 provides an ultrasound receive signal or data during the insertion, use or operation of an invasive medical device 11 (e.g. needle, biopsy needle or ablation probe) within the anatomical region A of the body of the patient. For example, the target T treated or targeted by the medical invasive device may be a carcinoma to be ablated in radio frequency ablation (RFA). When performing the image guidance procedure, the doctor must be able to visualize the target T in the anatomical region A, the invasive medical device 11 approaching the target T, and any vessels 15 surrounding the target T, in particular blood vessels or vasculature. Therefore, imaging of the vessels 15 is important for ensuring that no major vessel is punctured during the insertion and guidance of the invasive medical device 11.

Figure 3:
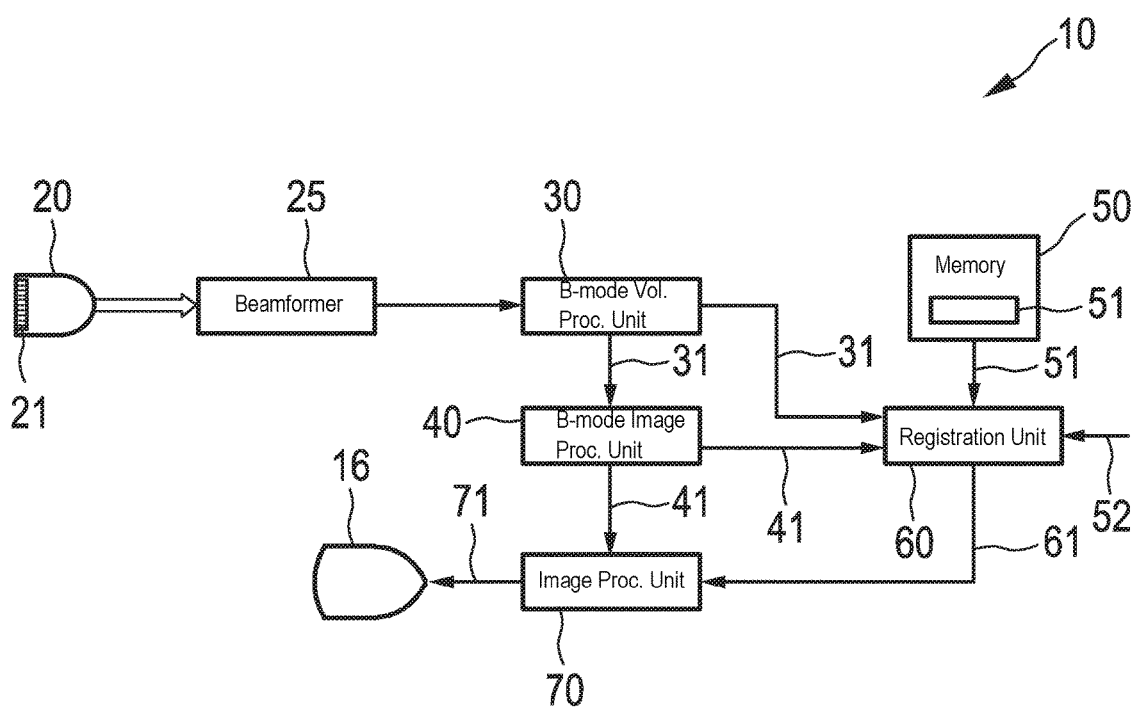
FIG. 3 shows a block diagram of an ultrasound imaging system according to a first embodiment.

FIG. 3 shows a block diagram of an ultrasound imaging system 10 according to a first embodiment. The ultrasound imaging system 10 comprises an ultrasound probe 20 having a transducer array 21 configured to provide an ultrasound receive signal. The transducer array 21 can in particular be a 2D transducer array. The ultrasound imaging system 10 of FIG. 1 comprises a beamformer 25 connected to the ultrasound probe 20 and its transducer array. The beamformer 25 receives an ultrasound receive signal or data from the transducer array 21 and performs beamforming. In this way many 2D scans or frames that lie one next to one another are acquired which are then sent to a B-mode volume processing unit 30 to form a 3D-volume 31 of data. Thus, in the embodiment shown in FIG. 3, as well as in the following embodiments, electronic scanning of the volume in the anatomical region is used. However, it will be understood that the system could alternatively also use mechanically scanning.

As mentioned, the ultrasound imaging system 10 comprises the B-mode volume processing unit 30 configured to generate, using signal processing, a B-mode volume 31 based on the ultrasound receive signal or data received from the beamformer 25. Further, the system 10 comprises a B-mode image processing unit 40 configured to provide a current B-mode image 41 to be displayed, based on the B-mode volume 31, by image processing. Even though a 3D B-mode volume of data is generated by the B-mode volume processing unit 30, the actual presentation or displaying of data does not necessarily need to be also 3D. For example, for a non-fluid filled structure, in some cases a rendered 3D-image may not be the most useful way to present the data, and a 2D image or orthogonal 2D-image planes through the volume may be easier for the user to interpret. In particular, the current B-mode image can be a 2D-image, thus a slice of the 3D B-mode volume, or can be an (3D-) image of orthogonal 2D-image planes, e.g. Multi-Planar Reformatted (MPR) which are an axial, sagittal and coronal planes. Alternatively, the current B-mode image (to be displayed) can of course also be a 3D-image. In this case, a 3D-image 41 of the volume of interest is built out of the 3D-volume 31 of data. This provides the most possible information to the user.

Figure 5:
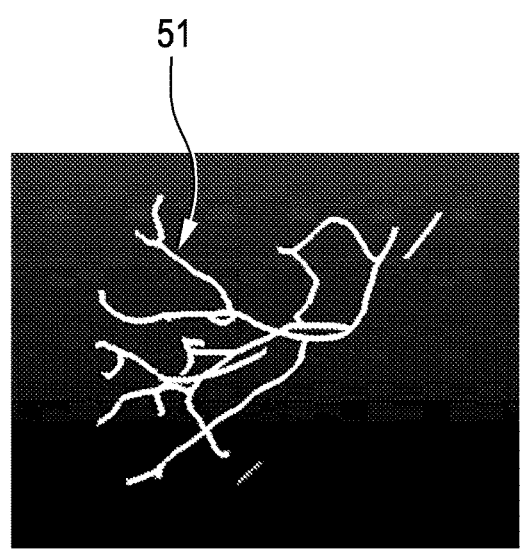
FIG. 5 shows an exemplary 3D-vessel map.

Further, the ultrasound imaging system 10 comprises a memory 50 configured to store a previously acquired 3D-vessel map 51. This means that a 3D-vessel map 51 of the anatomical region is acquired or created at the beginning or before an ultrasound image guidance procedure. Since the 3D-vessel map is acquired at the beginning of the ultrasound image guidance procedure, prior to actually inserting the invasive medical device into the patient, time can be taken to acquire the highest possible quality 3D-vessel map. FIG. 5 shows an example of such a 3D-vessel map 51, in this case of a liver. It will be understood that the specific vessel map of a liver in FIG. 5 is merely exemplary and that any other suitable vessel map can be used, for example of another organ, in particular an organ that can be imaged using ultrasound.

The frame rates during the acquisition of the 3D-vessel map 51 may be slow, but since the 3D-vessel map 51 is acquired at the beginning or before the ultrasound image guidance procedure, the frame rate during the ultrasound image guidance procedure itself, using B-mode imaging as explained above, is not effected. Thus, since the current or live acquisition of B-mode images, using the B-mode volume processing unit 30 and the B-mode image processing unit 40 as explained above, only involves B-mode, high or real-time frame rates can be achieved.

The ultrasound imaging system 10 comprises a registration unit 60 configured to register the previously acquired 3D-vessel map 51 to the B-mode volume 31. Any suitable method or technique for performing such registration can be used. In one specific non-limiting example, a registration technique as disclosed in "Automatic Non-Linear Mapping of Pre-Procedure CT Volumes to 3D Ultrasound, Wein et al., IEEE International Symposium on Biomedical Imaging (ISBI), Rotterdam, 2010", which is incorporated herein by reference, can be used. In another specific non-limiting example, a registration technique as disclosed in "Three-Dimensional Registration and Fusion of Ultrasound and MRI Using Major Vessels as Fiducial Markers, Porter et al., IEEE Trans Med Imaging 2001, 20(4), pp. 354-359", which is incorporated herein by reference, can be used. In a further specific non-limiting example, a registration technique as disclosed in "Vessel-Based Non-Rigid Registration of MR/CT and 3D Ultrasound for Navigation in Liver Surgery, Lange et al., Computer Aided Surgery, 8:228-240 (2003)", which is incorporated herein by reference, can be used.

Furthermore, the registration unit 60 is configured to select a or at least a portion 61 of the 3D-vessel map corresponding to the current B-mode image 41. In one example, if the current B-mode image 41 is a 2D-image or an image of orthogonal 2D-image planes, as explained above, the portion 61 is a 2D-slice of the 3D-vessel map 51. Thus, if the B-mode volume 31 is sliced to get a 2D B-mode image 41 for display, also the 3D-vessel map 51 is sliced in the same way. In an alternative example, if the current B-mode image 41 is a 3D-image, the portion is a 3-D portion of the 3D-vessel map 51. Thus, if a 3D B-mode image 41 is to be displayed, the 3D-vessel map 51 is superimposed in the same way. In another example, the portion 61 of the 3D-vessel map is the entire 3D-vessel map. Thus, in this example, the entire stored 3D-vessel map or information is displayed.

Preferably or optionally, the 3D-vessel map is tracked, i.e. continuously updated, as the ultrasound image guidance procedure takes place. In this case, the registration unit 60 is configured to receive ultrasound transducer position tracking information 52 for selecting the portion 61 of the 3D-vessel map 51 corresponding to the current B-mode image 41. In other words, the portion 61 is selected using the received ultrasound transducer position tracking information 52. The ultrasound transducer position tracking information 52 indicates and/or tracks the position of the ultrasound probe 20 having the transducer array 21, or also called ultrasound transducer. The ultrasound transducer position tracking information 52 is used to select the portion 61 and/or to continuously update the registration. The use of ultrasound transducer position tracking information will be explained in more detail with reference to the embodiments of FIG. 9 and FIG. 10.

Optionally, the ultrasound system 10 may also comprises an image processing unit 70 configured receive the current B-mode image 41 and the selected portion 61 of the 3D-vessel map 51 to provide an ultrasound image 71 with vessel information, which can then be displayed.

The ultrasound imaging system 10 further comprises a display 16 configured to display the ultrasound image 71. The ultrasound image 71 is based on the current B-mode image 41 and the selected portion 61. In this way the user of the system (e.g. doctor or clinician) can use the displayed ultrasound image 71 with vessel information during an image guidance procedure, as for example explained with reference to FIG. 2. As explained above, the ultrasound image 71 or current B-mode image 41 to be displayed can either be a 2D- or 3D-image.

Figure 11:
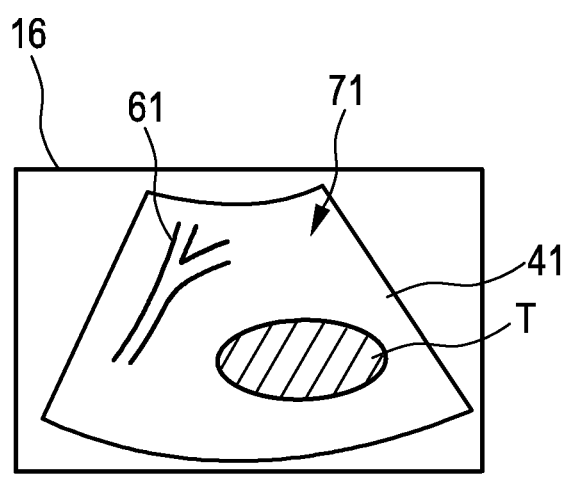
FIG. 11 shows one example of a display with an ultrasound image with vessel information.
Figure 12:
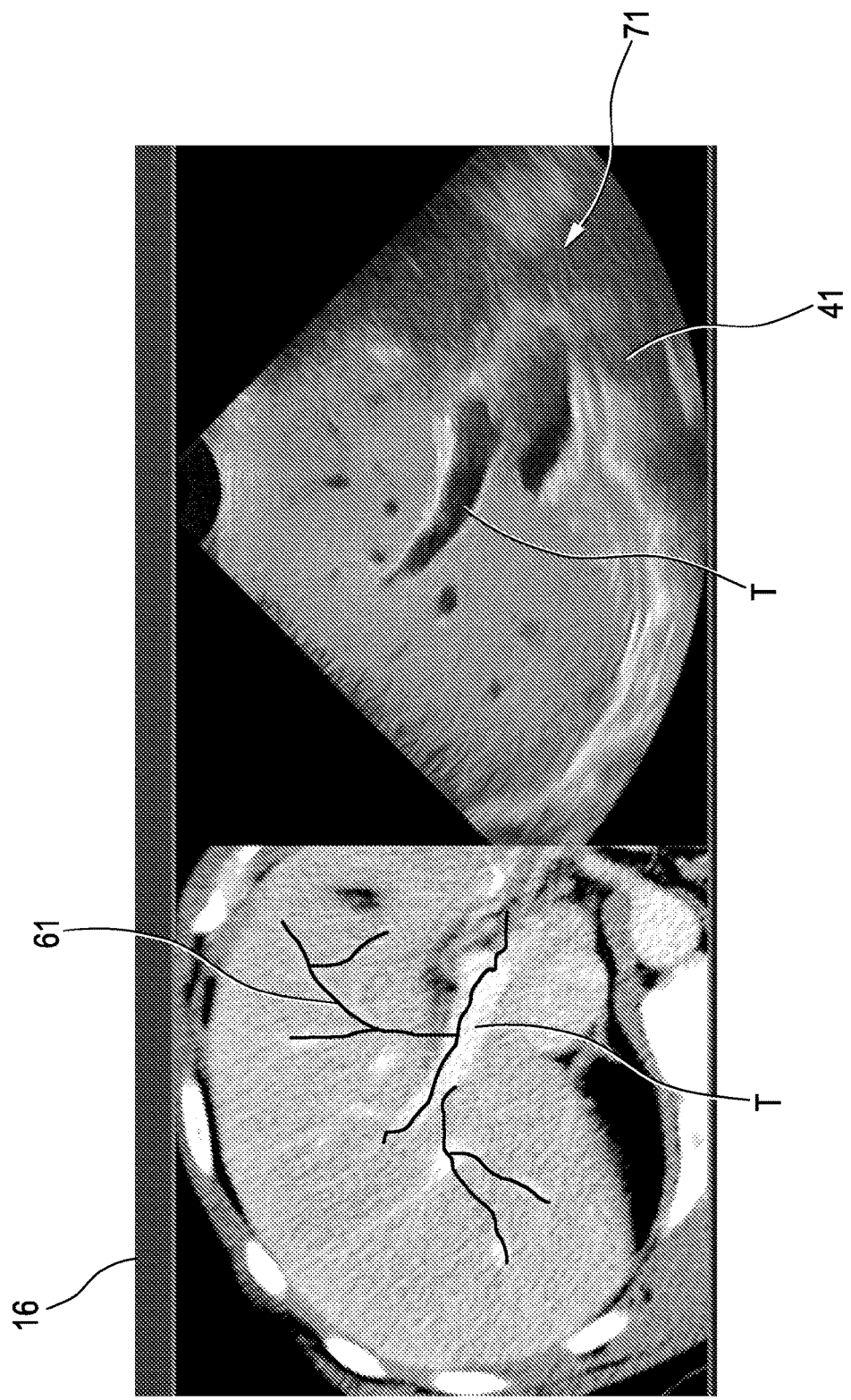
FIG. 12 shows another example of a display with an ultrasound image with vessel information.

FIG. 11 shows, in form of a schematic diagram, one example of a display 16 with an ultrasound image 71 with vessel information. FIG. 12 shows, in form of a picture, another example of a display 16 with an ultrasound image 71 with vessel information. In each of the examples of FIG. 11 and FIG. 12, the ultrasound image 71 or current B-mode image 41 is a 2D B-mode image illustrating the target T in the anatomical region of interest. In this case, the portion 61 is a 2D-slice of the 3D-vessel map, as can be seen in FIG. 11 or FIG. 12. The invasive medical device (not shown in FIG. 11 or FIG. 12) may also be visible in the image during an image guidance procedure.

In the example of FIG. 11, the ultrasound image 71 is provided by overlaying the current B-mode image 41 and the selected portion 61 of the 3D-vessel map. In this case, the image processing unit 70 is configured to overlay or fuse the current B-mode image 41 and the selected portion 61 of the 3D-vessel map 51 to provide the ultrasound image 71 with overlaid vessel information, which can then be displayed. Thus, the ultrasound image 71 has overlaid vessel information. In other words, the vessel information or portion of the 3D-vessel map 61 is directly overlaid onto or incorporated into the ultrasound image. The ultrasound image 71 comprises vessel information, overlaid on the 2D B-mode image 41, in the form of the portion 61 of the 3D-vessel map. In this example of FIG. 11, the vessel information or portion 61 is illustrated in form of the outlines of the vessel. However, it will be understood that the vessel information can be presented in any other suitable manner, such as for example a line running along the center of the vessel or colorizing the vessel within the boundaries of the outline.

In the example of FIG. 12, the ultrasound image 71 is provided by having the current (or live) B-mode image 41 and the selected portion 61 of the 3D-vessel map in a side by side format or representation. In FIG. 12, the current (or live) B-mode image 41 is presented as a first image portion on the right side of the display 16 and the selected portion 61 is presented in a second image portion on the left side of the display 16. In this case, the image processing unit 70 is configured to add the current B-mode image 41 and the selected portion 61 of the 3D-vessel map 51 next to each other to provide the ultrasound image 71 with vessel information, which can then be displayed. The selected portion 61 or vessel information can for example be in a previously acquired registered image (e.g. color image). In one example, the selected portion 61 can be presented or contained in CT data or MR data (see FIG. 12), as will be explained in further detail with reference to FIG. 8. In another example, the selected portion 61 can be presented or contained in an ultrasound image, as will be explained in further detail with reference to FIG. 6 or FIG. 7. In this example of FIG. 12, the vessel information or portion 61 is illustrated in form of a line running along the center of the vessel. However, as mentioned above, it will be understood that the vessel information can be presented in any other suitable manner.

It will be understood that the displays shown in FIG. 11 and FIG. 12 are specific examples, and that the ultrasound image with vessel information can be displayed in any other suitable manner. In any case, the doctor or user looking at the display 16 is able to see the vessel information and the B-mode image 41 which helps to avoid the vessels during the image guidance procedure. Therefore, on the display 16 a portion of the registered vessel map that moves with the current or live B-mode image 41 can be observed. The fact that it is a previously acquired 3D-vessel map instead of something acquired live is visible from seeing that the vessels do not pulsate, and just move and rotate with the position of the ultrasound probe 20. Optionally, a message could be provided on the display that informs the user that the vessel and flow information is not live.

Further embodiments will now be explained with reference to FIG. 6 to FIG. 10. As each of the embodiments of FIG. 6 to FIG. 10 is based on the first embodiment of FIG. 1, the same explanations as to the embodiment of FIG. 1 also apply to the embodiments of FIG. 6 to FIG. 10.

Figure 6:
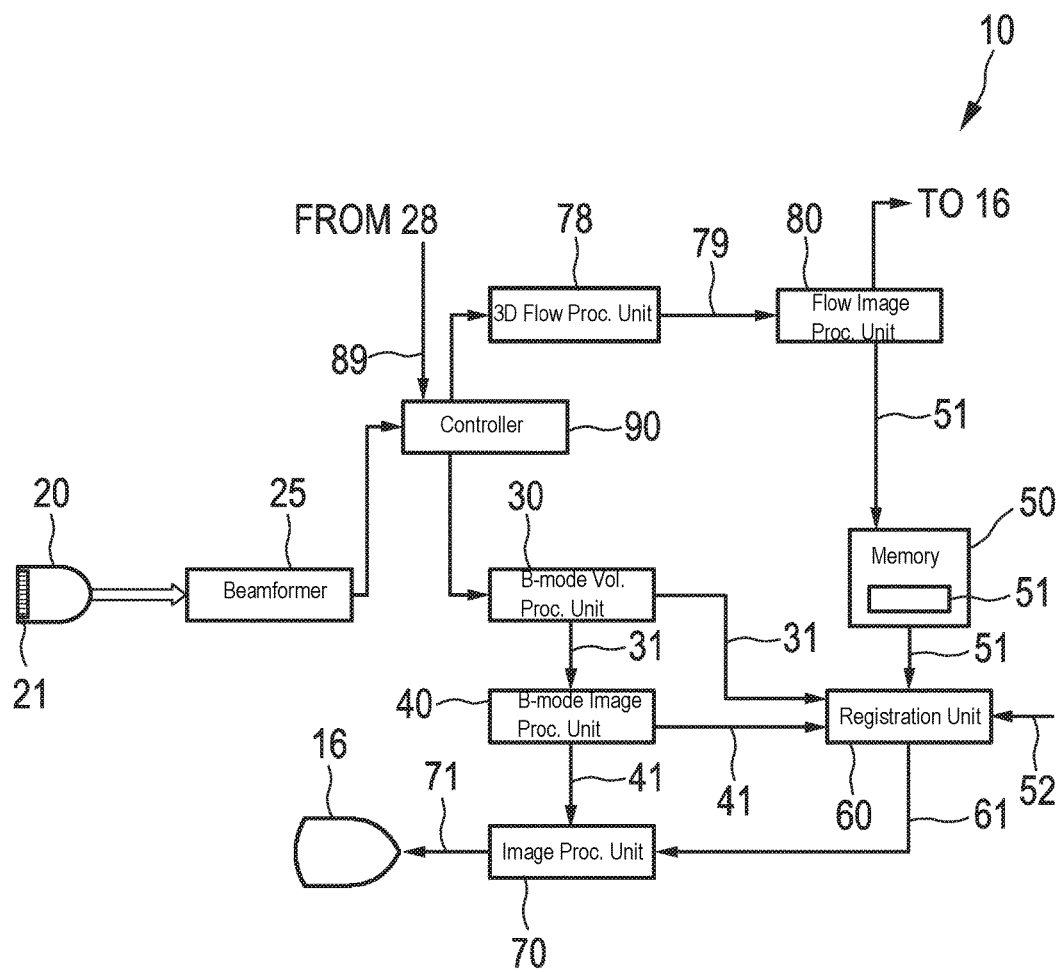
FIG. 6 shows a block diagram of an ultrasound imaging system according to a second embodiment.

FIG. 6 shows a block diagram of an ultrasound imaging system according to a second embodiment, in which the vessels or vasculature in the anatomical region are identified using a 3D flow imaging technique. In the embodiment of FIG. 6, the ultrasound imaging system 10 additionally comprises a 3D flow processing unit 78 configured to generate 3D flow data 79 based on the ultrasound receive signal, and a flow image processing unit 80 configured to generate the 3D vessel map 51 based on the 3D flow data 79. 3D flow data 79 (or also called flow volume) can be generated in that the transducer array 21 transmits multiple ultrasound pulses for each line in order to estimate the flow at that line. Then, the acquisition of these lines is swept across the volume. The number of ultrasound pulses may be increased. This increases the sensitivity, but also reduces the frame rates. For example, the 3D flow processing unit 78 can be configured to generate the 3D flow data 79 using a color flow technique, a Color Power Angio (CPA) technique or a B-mode flow imaging technique. In the case of CPA, the generated flow image or 3D-vessel map indicates only the magnitude of the flow, and not directionality of the flow. In the case of B-mode flow imaging (also called B-flow), the flow image is generated using a B-mode pulse subtraction technique. Also, the 3D flow processing unit 78 can be configured to generate the 3D flow data 79 using a Contrast Enhanced Ultrasound technique. This is a particularly suitable way to improve the visualization of the vessels, especially in technically challenging cases. It will be understood that in fact any technique for visualizing or reconstructing a 3D flow image can be used.

In the embodiment of FIG. 6, the ultrasound imaging system 10 further comprises a controller 90 configured to select either the B-mode volume processing unit 30, so that it generates the B-mode volume 31, or the 3D flow processing unit 78, so that it generates the 3D flow data 79. In particular, the controller is configured to first select the 3D flow processing unit 78, so that the 3D-vessel map 51 can be acquired before or at the beginning of an image guidance procedure, and to the subsequently select the B-mode volume processing unit, so that B-mode imaging can be used during the image guidance procedure. When the controller 90 selects the 3D flow processing unit 78, the 3D flow data 79 can be generated in that the transducer array 21 transmits multiple ultrasound pulses for each line, and then the acquisition of these lines is swept across the volume. When the controller 90 selects the B-mode volume processing unit 30, the B-mode volume 31 can be generated in that the transducer array 21 transmits a single pulse for each line, and then the acquisition of these lines is swept across the volume. The selection performed by the controller 90 can in particular be achieved based on user input 89. Thus, the controller 90 can be connected to user controls 28 for receiving user input 89, such as for example user controls 28 of FIG. 1. The controller 90 can then be configured to select the 3D flow processing unit 30 when receiving a first user input 89a from the user controls 28 (e.g. when a user hits a "Start" button) and to select the B-mode volume processing unit 30 when receiving a second user input 89b from the user controls 28 (e.g. when the user hits an "Accept" button). Optionally, the flow image or 3D-vessel map 51 may also be displayed alone or separately on a display 16. Therefore, as indicated in FIG. 6, the flow image or 3D-vessel map 51 can be transmitted to the display 16.

Now, for a better understanding, a specific application case of using the system 10 will be given. The user places the ultrasound probe 20 having the 2D transducer array 21 in the desired scan window that permits visualization of the target T and the path of the needle 11. Prior to inserting the needle 11, the user hits a "Start" button on the user controls 28. This initiates the acquisition of a high-quality color flow volume data. The user then hits an "Accept" button on the user controls if the color flow volume data provides the desired 3D-vessel map (e.g. displayed on display 16). Upon accepting, the system 10 immediately starts acquisition of a B-mode volume at much higher volume rates than with the color 3D flow data or flow volume. Then, some type of anatomical feature tracking or speckle tracking may be applied to consecutive B-mode volumes. This provides information about how much translation and rotation is happening from volume to volume. This translation and rotation is applied to the 3D-vessel map based on the color 3D flow data or flow volume, so that the 3D-vessel map stays registered to what the B-mode image is showing. This vessel map is overlaid onto the current or live B-mode image, for example in a different tint. The needle guidance then takes place, either with a 2D-slice of the B-mode volume, an image of orthogonal 2D-image planes (e.g. MPRs), or using the 3D rendered view. Regardless of the way the B-mode volume is sliced and presented, the registered 3D vessel map can be sliced and presented in the same way.

Figure 4:
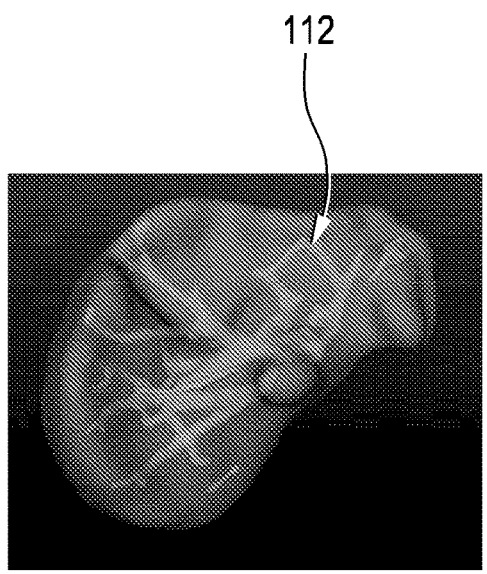
FIG. 4 shows an exemplary CT data set.
Figure 7:
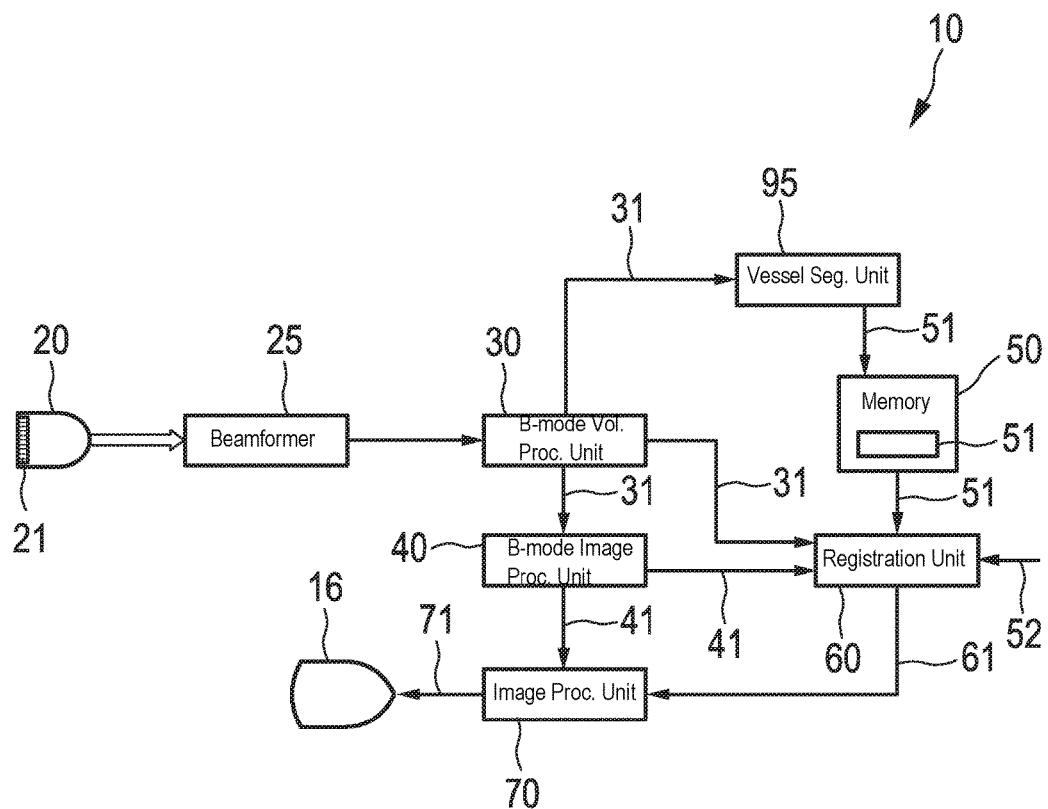
FIG. 7 shows a block diagram of an ultrasound imaging system according to a third embodiment.
Figure 8:
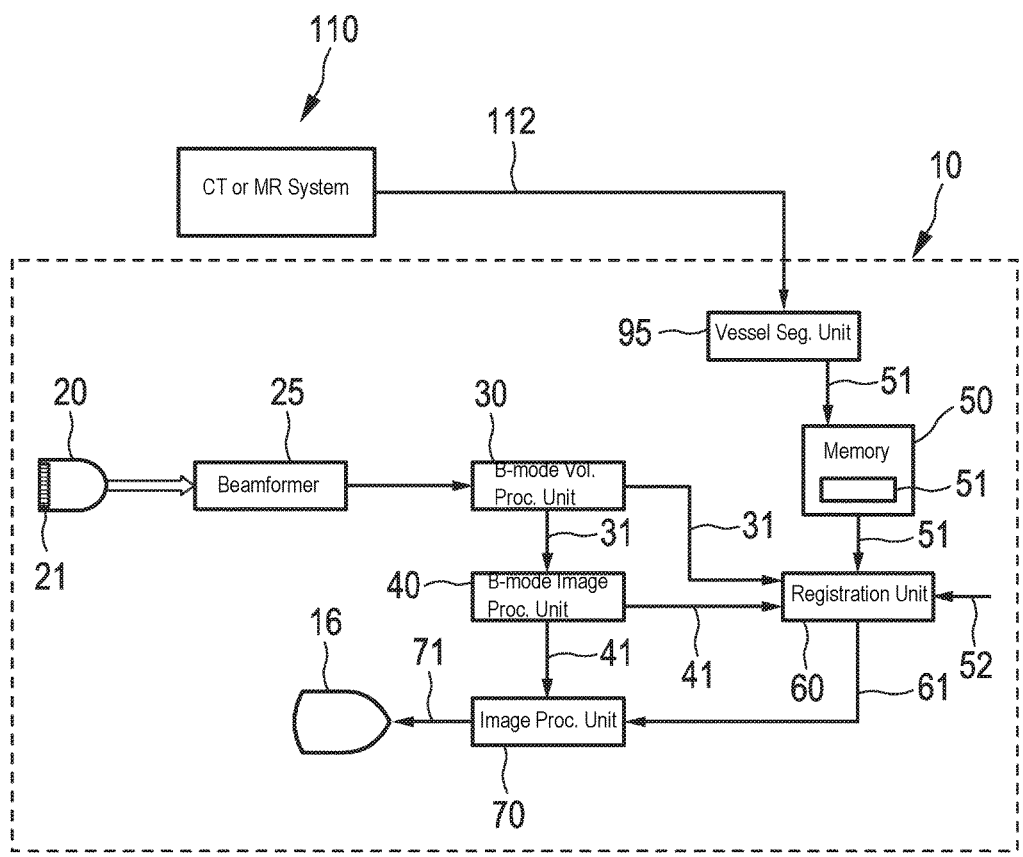
FIG. 8 shows a block diagram of an ultrasound imaging system according to a fourth embodiment.

FIG. 7 shows a block diagram of an ultrasound imaging system 10 according to a third embodiment, and FIG. 8 shows a block diagram of an ultrasound imaging system according to a fourth embodiment. In these embodiments, instead of using a flow acquisition technique as explained with reference to the embodiment of FIG. 6, a 3D vessel segmentation technique based on image data is used to generate the 3D vessel map 51. In each of the embodiments of FIG. 7 and FIG. 8, the ultrasound imaging system 10 therefore comprises a vessel segmentation unit 95 configured to create the 3D-vessel map 51 by performing a vessel segmentation technique. The vessel segmentation technique may for example be a technique as disclosed in WO 2006/085254 A1 or U.S. Pat. No. 7,870,189 B2, which is incorporated by reference herein. For example, the exemplary vessel map or tree shown in FIG. 4 is based on the vessel segmentation technique disclosed in WO 2006/085254 A1 or U.S. Pat. No. 7,870,189 B2.

In the embodiment of FIG. 7, the vessel segmentation unit is configured to perform the vessel segmentation technique based on the B-mode volume. In this case the 3D-vessel map is created based on 3D ultrasound data, namely the B-mode volume data that the system needs to acquire anyway. This provides for a particular easy way of creating the 3D-vessel map without the use of any other system or data. The B-mode volume can for example be conventional 3D ultrasound data or contrast enhanced 3D ultrasound data.

Instead of using 3D ultrasound data, the vessel segmentation unit 95 can be configured to perform the vessel segmentation technique based on CT data or MR data 112, as illustrated in the embodiment of FIG. 8. In this embodiment the vessel segmentation unit 95 is configured to receive the CT or MR data 112 from a separate CT or MR system 110 connected to the ultrasound imaging system 10. Thus, in this embodiment the 3D-vessel map 51 is created based on CT or MR data 112 received from the separate CT or MR system 110. However, it will be understood that the CT or MR data 112 can be received in any other suitable way, for example on a portable storage medium or by a CT or MR functionality within the ultrasound imaging system itself. The CT data can for example be conventional CT data, cone beam CT data, or CT angiography data. The MR data can for example be conventional MR data or MR Angiography data. The CT or MR data may also be acquired with or without a contrast agent or contrast agents.

FIG. 4 shows an exemplary CT data set 112, and FIG. 5 shows an exemplary 3D-vessel map 51, in particular created from the CT data set 112 of FIG. 4 using a vessel segmentation technique. As can be seen in FIG. 5, the 3D-vessel map 51 shows the outlines of the vessels, and can also be referred to as "wire frame".

Figure 9:
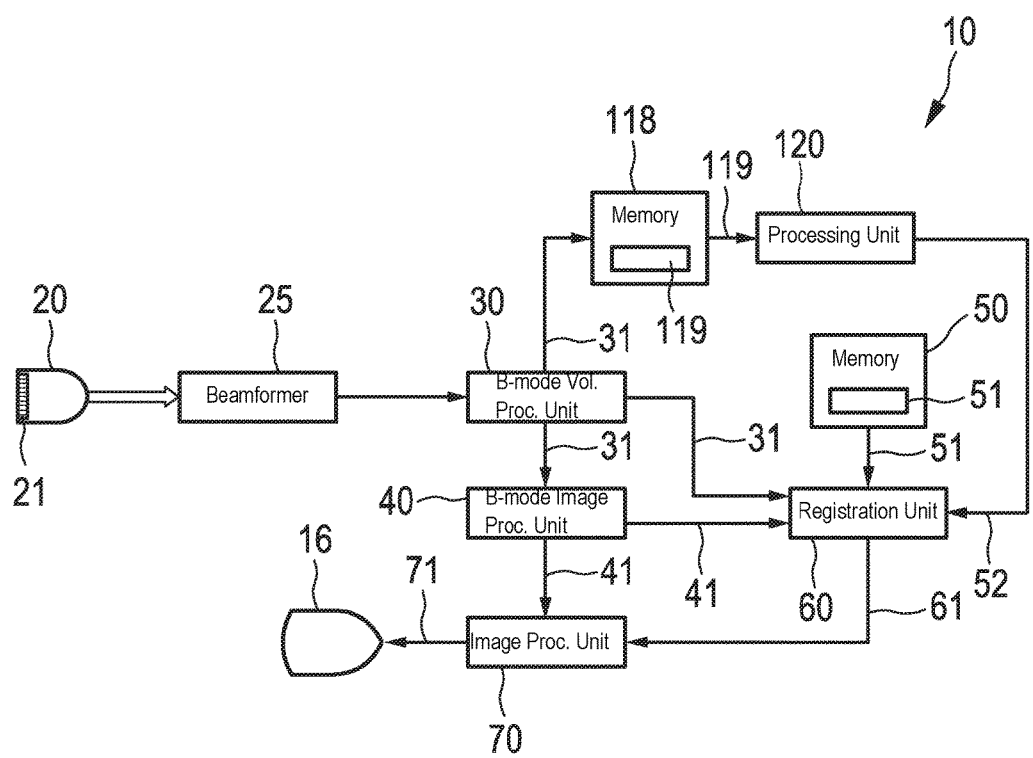
FIG. 9 shows a block diagram of an ultrasound imaging system according to a fifth embodiment.
Figure 10:
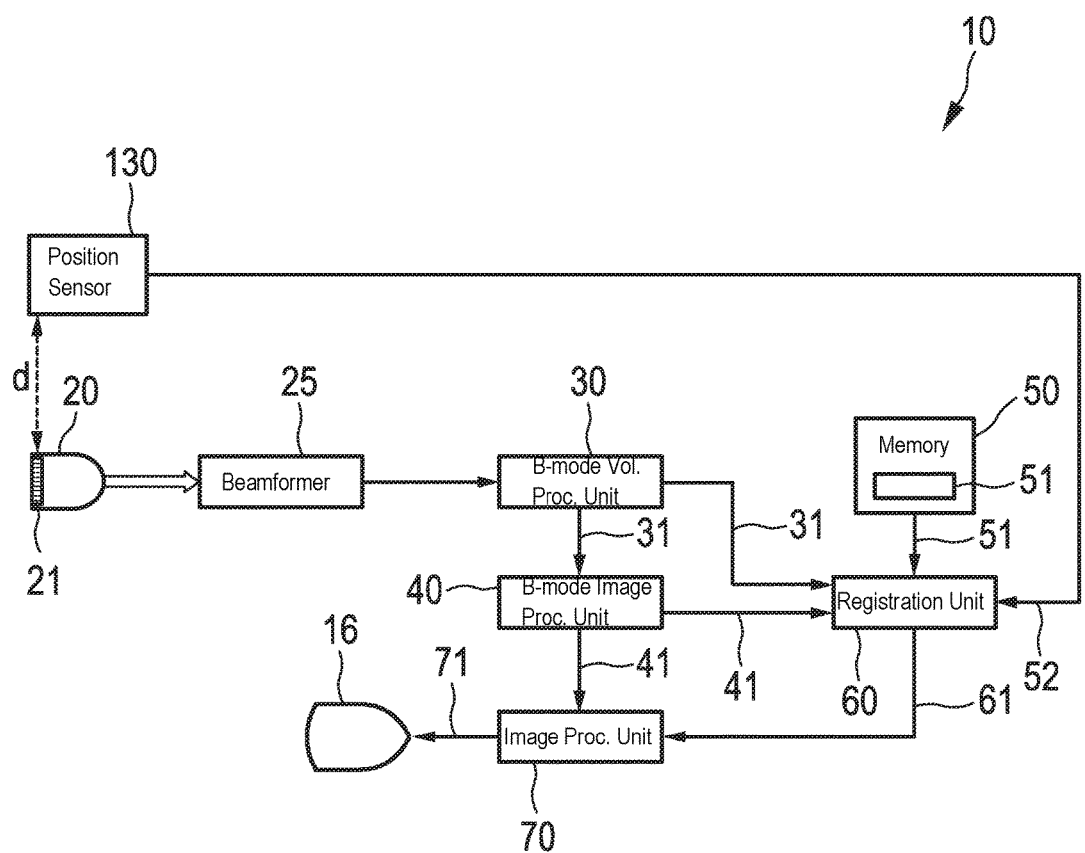
FIG. 10 shows a block diagram of an ultrasound imaging system according to a sixth embodiment.

FIG. 9 shows a block diagram of an ultrasound imaging system according to a fifth embodiment, and FIG. 10 shows a block diagram of an ultrasound imaging system according to a sixth embodiment. FIG. 9 and FIG. 10 each shows an embodiment of how the ultrasound transducer position tracking information 52, as explained with reference to the first embodiment of FIG. 3, can be generated. In each of FIG. 9 and FIG. 10, the registration unit 60 is configured to receive the ultrasound transducer position tracking information 52 for selecting the portion 61 of the 3D-vessel map corresponding to the current B-mode image 41, as explained with reference to the first embodiment of FIG. 3. It will be understood that the embodiment of FIG. 9 or FIG. 10, which is focused on the generation of ultrasound transducer position tracking information, can be combined with any of the embodiments of FIG. 3, FIG. 6, FIG. 7 or FIG. 8.

In the embodiment of FIG. 9, the ultrasound transducer position tracking information is generated using an image data based technique, in particular using feature tracking. Thus, the embodiment of FIG. 9 uses image-based tracking. In this case the ultrasound transducer position tracking information 52 is provided based on 3D ultrasound data, namely the B-mode volume data 31 that the system needs to acquire anyway. The term temporally consecutive can refer to B-mode volumes being acquired directly following each other or can refer to B-mode volumes being acquired not directly following each other, thus being spaced apart in time (e.g. only every other or every third volume). In the embodiment of FIG. 9, the ultrasound imaging system 10 further comprises a processing unit 120 configured to generate the ultrasound transducer position tracking information 52 based on temporally consecutive B-mode volumes. In the embodiment of FIG. 9, the ultrasound imaging system 10 also comprises a memory 118 for storing the B-mode volumes consecutive in time. The B-mode volumes 31 generated by B-mode volume processing unit 31 are transmitted one after the other to the memory 118 for storage. The processing unit 120 then receives and processes the temporally consecutive B-mode images 119. In particular, the processing unit 120 can be configured to perform feature tracking on the temporally consecutive B-mode volumes 119 and to generate a translation and/or rotation vector based on the feature tracking. In this case, the ultrasound transducer position tracking information 52 is then the translation and/or rotation information based on the translation and/or rotation vector. Thus, the translation and/or rotation of features in the temporally consecutive B-mode volumes 119 is tracked and based thereon a translation vector or rotation vector is extracted. In the case of generating the ultrasound transducer position tracking information based on consecutive B-mode volumes, as shown in the embodiment of FIG. 9, the B-mode volume processing unit 30 has to generate the 3D B-mode volumes continuously during the image guidance procedure (or scanning of the body with the ultrasound probe). In this way there is continuously underlying B-mode volume data to generate the translation information from. This continuous generation also applies for a case where the current B-mode image to be displayed is only a 2D-image.

Instead of using feature tracking on temporally consecutive B-mode volumes (i.e. image-based tracking) to figure out how much to translate and/or rotate the 3D-vessel map 51, a position sensor 130 can be used, as indicated in the embodiment of FIG. 10. The embodiment of FIG. 10 thus shows a sensor-based tracking approach. As can be seen in FIG. 10, the position sensor 130 is positioned in fixed known position with respect to the ultrasound probe 20 having the transducer array 21, for example arranged on or attached to the housing on the probe 20. The ultrasound transducer position tracking information 52 is position information received from the position sensor 130. The position sensor 130 can be used to track the orientation and/or positional changes of the ultrasound probe 20 or transducer array 21. If the ultrasound transducer position tracking information is generated based on a position sensor, as shown in the embodiment of FIG. 10, the B-mode processing unit 30 does not need to generate the 3D B-mode volumes continuously in a case where the current B-mode image to be displayed is only a 2D-image. However, if the current B-mode image to be displayed is a 3D-image, the B-mode processing unit 30 has to generate the 3D B-mode volumes continuously.

For example, the position sensor can be an electromagnetic (EM) tracking sensor or a fiber optic tracking sensor. However, it will be understood that in general any sensor can be used that provides tracking information about the transducer position. Any ultrasound probe having a 2D transducer array (e.g. the X6-1 probe) and having an EM tracking sensor is capable of generating a calibrated volume of B-mode and color flow data.

Figure 13:
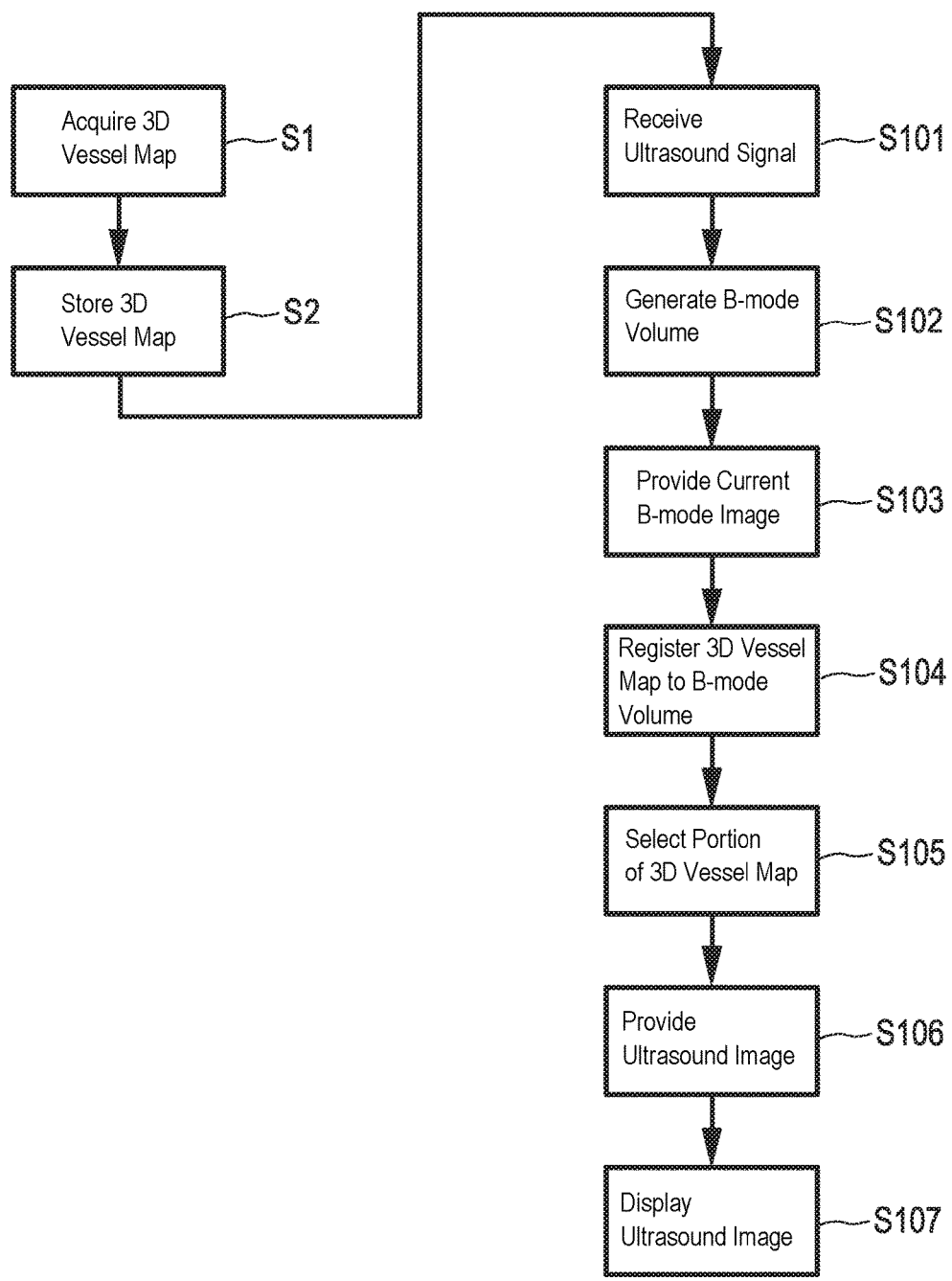
FIG. 13 shows a block diagram of a method for generating an ultrasound image with overlaid vessel information according to an embodiment.

Now, the corresponding method for providing an ultrasound image with vessel information will be explained with reference to FIG. 13 which shows a block diagram of such a method according to an embodiment, in particular corresponding to the first basic embodiment of FIG. 3. In a first step S1, a 3D-vessel map 51 is acquired. This is in particular done before or at the beginning of an image guidance procedure. Then, as indicated in step S2, the 3D-vessel map 51 is stored in a memory 50. Next, the method comprises the step of receiving, in step S101, an ultrasound receive signal provided by an ultrasound probe 20 having a transducer array 21. Subsequently, in step S102, a B-mode volume 31 based on the ultrasound receive signal is generated and, in step S103, a current B-mode image 41 based on the B-mode volume 31 is provided. Then, in step S104, the method comprises registering the previously acquired 3D-vessel map 51, stored in the memory 50, to the B-mode volume 31. Furthermore, the method comprises selecting, in step S105, a portion 61 of the 3D-vessel map 51 corresponding to the current B-mode image 41. Subsequently, in step S106, the method comprises providing the ultrasound image 71 based on the current B-mode image 41 and the selected portion 61 of the 3D-vessel map 51. In one specific example, the ultrasound image 71 can be provided by overlaying or fusing the current B-mode image 41 and the selected portion 61, as explained with reference to the example of FIG. 11. In another specific example, the ultrasound image 71 can be provided by having the current (or live) B-mode image 41 and the selected portion 61 in a side by side format or representation. Finally, the ultrasound image 71 with vessel information may then be displayed on a display 16 in step 107. These steps can for example be performed in one or more processors (e.g. microprocessors).

In general, it will be understood that the different (processing) units described herein can be implemented in any suitable way in hardware or software. Any one or more (processing) units 25, 30, 40, 60, 70, 90, 78, 80, 95, 120 as described herein, in particular with respect to any one of the embodiments of FIG. 3 or FIGS. 6 to 10, can be implemented in one or more processors (e.g. microprocessors). For example, the B-mode volume processing unit 30, the B-mode image processing unit 40, the registration unit 60, and optionally the image processing unit 70, can be implemented in one single or multiple processors.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An ultrasound imaging system comprising:
an ultrasound probe having a transducer array configured to provide an ultrasound receive signal,
a B-mode volume processing unit configured to generate a B-mode volume based on the ultrasound receive signal,
a B-mode image processing unit configured to provide a current B-mode image based on the B-mode volume,
a vessel segmentation unit configured to create a 3D-vessel map by performing a vessel segmentation technique prior to insertion of an invasive device during an ultrasound image guidance procedure,
a memory configured to store the 3D-vessel map,
a registration unit configured to automatically register the 3D-vessel map retrieved from the memory to the B-mode volume and to select a portion of the 3D-vessel map corresponding to
the current B-mode image, and wherein the registration unit is configured to receive ultrasound
transducer position tracking information and use the position tracking information to select the portion of the 3D-vessel map corresponding to the current B-mode image,
a display configured to display a live ultrasound image, which is updated in real-time during the insertion of the invasive device, based on the current B-mode image and the selected portion of the 3D-vessel map, and
an image processing unit configured to overlay the current B-mode image and the selected portion of the 3D-vessel map to provide the live ultrasound image.

2. The ultrasound imaging system of claim 1, wherein the current B-mode image is a 2D-image or an image of orthogonal 2D-image planes.

3. The ultrasound imaging system of claim 1, wherein the portion is a 2D-slice of the 3D-vessel map or a 3-D portion of the 3D-vessel map.

4. The ultrasound imaging system of claim 1, the vessel segmentation unit configured to perform the vessel segmentation technique based on a B-mode volume acquired with the ultrasound probe prior to the insertion of the invasive device.

5. The ultrasound imaging system of claim 1, the vessel segmentation unit configured to perform the vessel segmentation technique based on CT data or MR data.

6. The ultrasound imaging system of claim 1, further comprising a processing unit configured to generate the ultrasound transducer position tracking information using feature tracking on temporally consecutive B-mode volumes, and wherein the ultrasound transducer position tracking information is translation and/or rotation information.

7. The ultrasound imaging system of claim 1, further comprising a position sensor which is positioned in fixed known position with respect to the transducer array, and wherein the ultrasound transducer position tracking information is position information received from the position sensor.

8. The ultrasound imaging system of claim 1, wherein the current B-mode image is a 3D-image.

9. A method for providing an ultrasound image with vessel information, the method comprising:
  receiving ultrasound receive signals provided by an ultrasound probe having a transducer array,
  generating temporally consecutive B-mode volumes based on the ultrasound receive signals,
  providing a current B-mode image based on one of the temporally consecutive B-mode volumes and an updated current B-mode image based on another one of the temporally consecutive B-mode volumes,
  creating a 3D-vessel map by performing a vessel segmentation technique and storing the 3D-vessel map in memory,
  registering the 3D-vessel map retrieved from memory to the temporally consecutive B-mode volumes,
  receiving ultrasound transducer position tracking information,
  selecting respective portions of the 3D-vessel map corresponding to each of the current B-mode image and the updated current B-mode image, wherein the selecting includes using the position tracking information to select at least one of the respective portions of the 3D-vessel map,
  displaying a live ultrasound image based on the current B-mode image and the respective portion of the 3D-vessel map corresponding to the current B-mode image, which includes overlaying the current B-mode image and the respective portion of the 3D-vessel map to provide the ultrasound image by image processing, and
  updating the displayed image in real-time with an ultrasound image based on the updated current B-mode image and the respective portion of the 3D-vessel map corresponding to the updated current B-mode image.

10. A non-transitory computer readable medium comprising program code for causing a computer to carry out the steps of the method as claimed in claim 9 when said program code is carried out on the computer.

11. The method of claim 9, further comprising generating the ultrasound transducer position tracking information based on temporally consecutive B-mode volumes, and wherein the ultrasound transducer position tracking information is translation and/or rotation information.

12. The method of claim 11, wherein generating the ultrasound transducer position tracking information includes performing feature tracking on the temporally consecutive B-mode volumes to generate the ultrasound transducer position tracking information.

* * * * *